United States Patent [19]
Åhlén

[11] Patent Number: 5,767,975
[45] Date of Patent: Jun. 16, 1998

[54] METHOD AND DEVICE FOR DETECTING THE POSITION FOR A CREASE LINE OF A PACKAGING WEB

[75] Inventor: Hans Åhlén, Stockholm, Sweden

[73] Assignee: Tetra Laval Holdings and Finance, Pully, Sweden

[21] Appl. No.: 716,231

[22] PCT Filed: Mar. 17, 1995

[86] PCT No.: PCT/SE95/00269

§ 371 Date: Oct. 30, 1996

§ 102(e) Date: Oct. 30, 1996

[87] PCT Pub. No.: WO95/25941

PCT Pub. Date: Sep. 28, 1995

[30] Foreign Application Priority Data

Mar. 21, 1994 [SE] Sweden ................... 9400929

[51] Int. Cl.⁶ .................... G01N 21/84; G01N 21/00; G01N 21/86
[52] U.S. Cl. .................... 356/429; 356/430; 356/375; 356/394; 250/559.39; 250/559.4; 250/559.44; 250/359.45
[58] Field of Search .................... 356/375, 394, 356/429–431, 237, 239; 250/559.39, 40, 42, 44–46, 48–49

[56] References Cited

U.S. PATENT DOCUMENTS

| | | | |
|---|---|---|---|
| 3,125,265 | 3/1964 | Wamen et al. | 256/431 |
| 4,099,884 | 7/1978 | Nash | 250/559.45 |
| 4,184,770 | 1/1980 | Pinior | 256/430 |
| 4,450,352 | 5/1984 | Olsson | 250/223 R |
| 4,851,696 | 7/1989 | West | 250/559.16 |
| 5,115,144 | 5/1992 | Konishi et al. | 250/559.45 |
| 5,461,481 | 10/1995 | Boven et al. | 356/430 |

FOREIGN PATENT DOCUMENTS

60-236008   11/1985   Japan.

*Primary Examiner*—Frank G. Font
*Assistant Examiner*—Jason D. Vieera-Eisenberg
*Attorney, Agent, or Firm*—James Ray & Associates

[57] ABSTRACT

The position of a transverse crease line of a moving packing web is sensed in that light reflected from the web and emanating from a laser directed perpendicularly to the web is received by photo detectors from two directions in the direction of movement of the web and under an angle of for example 60° in relation to the light beam directed to the web. The electrical measuring signal emanating from the photo detectors is compared in an electronic signal processor with a reference signal, which is stored in the processor and is representative of a reference crease line. A crease line is indicated when the value of a correlation signal, which constitutes a calculation of conformity between the measuring signal and the reference signal, reaches a maximum. In a corresponding way, the position of a longitudinal crease line can be sensed.

20 Claims, 7 Drawing Sheets

FIG. 12 ately defined position in close proximity to a transverse crease line in order later to obtain the intended function of the finished package. Another example is when it is desired to decrease the width (for

METHOD AND DEVICE FOR DETECTING THE POSITION FOR A CREASE LINE OF A PACKAGING WEB

TECHNICAL FIELD

The present invention relates to a method for sensing the position of a crease line or similar embossment in a moving packaging web or the like. The invention also relates to a device for carrying out this method.

BACKGROUND OF THE INVENTION

A crease line in a packaging web can be regarded as a fold notch, along which a package, which is manufactured from the packaging web, is folded. Each package blank is thus provided with a number of crease lines, which can go in different directions on the packaging web.

In different cases there can be reasons to control a subsequent process based on a crease line, which can be transverse or longitudinal. One example is when a pull strip is to be placed in an accurately defined position in close proximity to a transverse crease line in order later to obtain the intended function of the finished package. Another example is when it is desired to decrease the width (for example from four to two packaging widths) of a packaging material with crease lines but without print. Presently, a longitudinal line is printed on the paper for controlling the cutting process. If it is possible to control a longitudinal crease line, the printing costs and the material waste for the black control line could be reduced.

Due to the difficulties to assess the position of a crease line, earlier attempts have been made to start from a characteristic part of the printed material on the packaging web; this printed material is regarded as being correctly positioned in relation to the crease lines. For different reasons the printing does not, however, obtain the right position in relation to the crease lines with satisfactory precision. This means, for example, that a pull strip, which is positioned in relation to the printing, is not necessarily at a correct position in relation to the intended crease line.

It is accordingly desirable to start from the primary element "the crease line" rather than the secondary element "the print" as the position of for example a pull strip.

A crease line is visible as a generally very weak embossment on the backside of a packaging web. A typical crease line can have a width of 1.8 mm and a height of only 0.03 mm. The crease line is further not especially well defined in its shape. The height of the crease line is further so small that irregularities of the packaging web can cause difficulties with the sensing of a crease line.

The difficulties to assess the position of a crease line in a packaging web are great at a web which is covered with aluminum, which rather often is the case, and even greater when not.

At the outset of the work leading up to the present invention a number of optical methods to sense crease lines were tested. Light was directed in different ways against a moving packaging web, and this light was received by means of photo detectors for creating a measuring signal. It appeared that several of these methods were completely impossible to continue with; a certain method could function for a web covered with aluminum but not for a web without aluminum.

It has already been said that a crease line has a very low height, that sometimes is hidden among normal surface irregularities, which means that it not only is a difficulty to obtain a signal from the crease line but also thereafter to treat this signal in such a way that a reliable and exact indication of the position of the crease line can be obtained.

The Invention

The solution to the problems mentioned above to sense the position of a crease line in a moving packaging web is according to the invention based on the principles:

that light, reflected from the packaging web and the crease line and emanating from a light beam directed against the web at an angle in relation to the reflected light, is received by means of at least one photo detector, which creates an electrical signal or picture of the packaging web and the crease line, that two electrical signals created by means of light from two directions are brought together to a measuring signal, which is compared in an electronic signal processor with a reference signal, which is stored in the processor and is representative for a reference crease line, and that a crease line is indicated, when the value of a correlation signal, which is a calculation of the conformity between the measuring signal and the reference signal, reaches a maximum.

This maximum must exceed a certain level in order to be approved as the correlation value for a crease line.

Differently speaking, an optical contrast method is utilized, where a part of the incoming light is collected by photo detectors, and a correlation measurement technique in an electronic signal processor. The light beam directed to the web is preferably created by a laser or a light diode and is given the form of a slot, and the angle between the incoming light beam and the light beam received by a photo detector is for example 60°. It is difficult to extract the exact position for the crease line by means of the measuring signals from the photo detectors. The signals contain much noise, especially from the paper structure. The crease lines are also of different magnitudes and in certain cases asymmetrical. Different paper qualities give different measuring signals.

In order to decrease the noise from the structure in the paper a difference signal from the electrical signals from the photo detector or the photo detectors is created. An even lower noise level is achieved in that the final measuring signal is formed as the quotient between the difference between the electrical signals and the sum thereof.

The crease signal is still fairly noisy, and there are no neat, well identifiable flanks to trig on. However, all crease signals generally have the form of an inclined N where the distance between positive top and negative bottom is constant and coupled to the widths of the crease line. This condition means that the position of a crease line can be identified with good accuracy by means of the correlation method mentioned above.

The principle for correlation measurement is that a measuring signal is compared to a reference signal and that the conformity between these two signals is calculated. There are several different algorithms for correlation measurement. The algorithm chosen for the method according to the invention gives as a result a correlation factor which is zero or negative if no correlation is found and positive if correlation is found.

In the method according to the invention the measuring signal is sampled with a certain feed length of the packaging web as basis. In a practical embodiment the feed length between pulses from a measuring wheel coupled to the packaging web is 80 µm, which at a speed of the packaging web not exceeding 350 m/min gives a distance between the center of the real crease line on the packaging web and the top of the correlation signal of 2.56 mm, whereas the signal which externally indicates a crease line is given after further 0.32 mm.

Accordingly, a top of the correlation signal indicating best conformity between the measuring signal and the reference signal will appear with a certain delay due to the length of the reference. When the top appears and based on the knowledge about the fixed distance difference to the indication of a crease line, the technique for sensing the position of a transverse crease line can for example be used for placing a pull tab in correct position in relation to a crease line with extremely good accuracy. Alternatively, the technique for sensing the position of a longitudinal crease line can for example be used as a position reference at cutting.

Practical solutions to the problems of sensing the position of a transverse crease line are given in claims 7 and 8, whereas practical solutions at sensing the position for a longitudinal crease line are given in claims 2 and 8.

The invention also relates to a device for carrying out the above discussed method of sensing the position for a crease line in a moving packaging web.

This device is according to the invention characterized by;

at least one light source for directing a light beam substantially perpendicular to the web, at least one photo detector for receiving light reflected from the packaging web from two directions transversely to the crease line and under a relatively great angle, for example 60°, in relation to the light beam directed to the web, and an electronic signal processor, in which an electrical measuring signal emanating from the photo detectors is compared with a reference signal, which is stored in the processor and is representative for a reference crease line, and in which a correlation signal is to be calculated and is a value on the conformity between the measuring signal and the reference signal and the maximum of which is an indication of a crease line.

The light source is preferably a laser or a light diode. The laser and the photo detectors can be arranged in a box. Preferred embodiments of a device for sensing the position of a transverse crease line are described in claim 7 with close space photo detectors, whereas preferred embodiments for sensing the position for a longitudinal crease line are described in claims utilizing an oscillating light.

The reasoning above is concentrated to the term "crease line", but it is obvious that the method and device according to the invention can be utilized for sensing the position of each inwardly or outwardly directed embossment of a web. It is also obvious that the method and device according to the invention can be utilized not only for sensing the position of the crease line but can also be utilized for assessing the appearance and also quality of the crease line.

BRIEF DESCRIPTION OF THE DRAWINGS

The invention will be described in more detail below reference being made to the accompanying drawings, in which.

DETAILED DESCRIPTION OF EMBODIMENTS

Two fundamentally different embodiments of the invention shall now be described under reference to the drawings, in which FIGS. 1–6 illustrate the invention utilized for sensing the position of a transverse crease line and FIGS. 7–12 illustrate the invention utilized for sensing the position of a longitudinal crease line.

Figure 1:
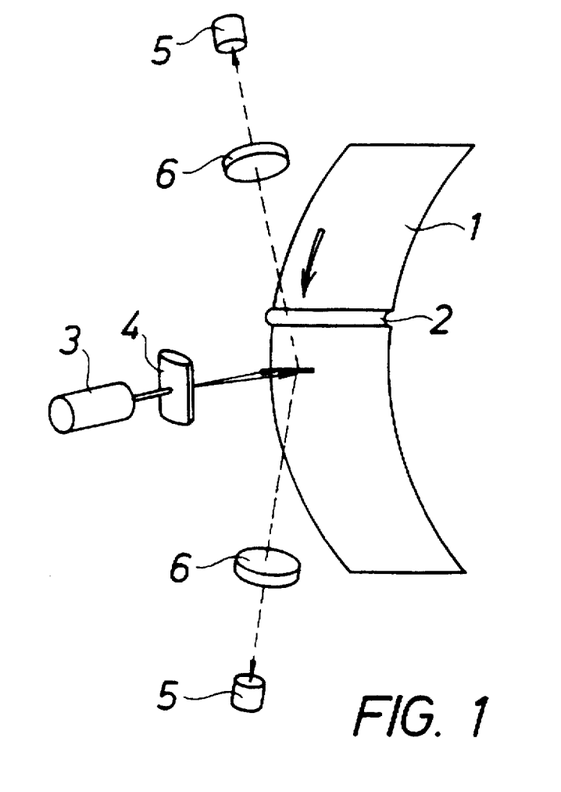
FIG. 1 illustrates an optical layout of a sensor device according to the invention for sensing the position for a transverse crease line, FIGS. 2A, B and C illustrate beam paths at the movement of a transverse crease line past a sensor according to the invention.

In FIG. 1 the reference numeral 1 is a packaging web, which can be arranged over a rotating cylinder, as illustrated, or can be movable over a plane surface. The packaging web 1 is provided with a transverse crease line 2, the position in the longitudinal direction of which it is desired to determine with great precision. The web 1 can be provided or not with an aluminum surface cover. As an alternative to a crease line 2 it is also possible to have any embossment directed inwardly or outwardly, but the term crease line is used throughout the description.

A crease line in a packaging web can be regarded as a fold notch and is embossed in the material by means of cooperating ridges and groves of two cylinders, between which the packaging web is transferred. A typical crease line can have a width of 1.8 mm and a height of 0.03 mm. The very low height means that the crease line can not be easily seen on a running packaging web, especially if the web is not aluminum covered and accordingly gives a certain contrast.

Theoretical considerations and practical tests have shown that the best results are achieved by means of a contrast method with optical sensing of angular variations on the surface of the packaging web, where light is directed perpendicularly against the surface and the reflected light is sensed from two directions under a great angle in relation to the approaching light. Alternatively it is possible to use the reversed beam path, i.e. light approaching obliquely from two directions and sensing generally perpendicular from the surface.

A device for carrying out this method is shown in FIG. 1. A laser 3 directs its light—for example visible red light—perpendicularly against the surface of the packaging web 1. A lens 4 (i.e. normally a group of lens elements) is arranged in the beam path of the laser 3 and has as its object to bring about a slot-formed, focused bundle of beams or rays on the packaging web 1. The slot has its longitudinal axis transverse to the movement direction of the packaging web and can have a length of for example 5 mm or more and a width of 0.1 mm.

The light reflected from the packaging web 1 is sensed by means of two photo detectors or photo diodes 5, to which the light can have been focused by means of lenses 6. The photo detectors 5 are arranged in the longitudinal direction of the packaging web 1 and can form an angle of for example 60° with the normal to the packaging web. The signals from the photo detectors 5—for example silicon detectors with a surface of 5 $mm^2$ —are treated electronically in a way described below.

Figure 2A:
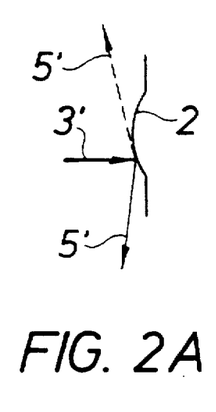

FIGS. 2 A–C illustrate roughly how the light 3' from the laser 3 is bounced back as reflected light 5' to the two photo detectors 5 at the passage of a crease line 2. In FIG. 2A the first part or the "uphill" of the crease line 2 is hit by the laser light 3'. In accordance with the normal optical reflection laws more reflected light 5' is reflected to the lower photo detector 5 than to the upper detector. In FIG. 2B the top of the crease line is hit by the laser light, and roughly the same amount of light is reflected to both photo detectors. In FIG. 2C finally the crease line has moved so far that the final part or "downhill" is hit by the laser light; in this case more light will be reflected to the upper detector than the lower detector.

Figure 3:
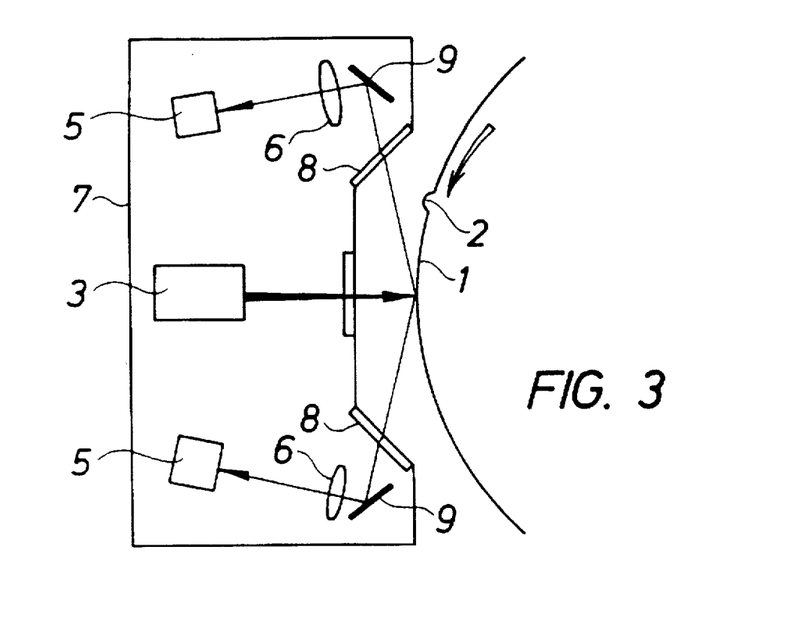
FIGS. 3 and 4 show two examples of practical embodiments of an optical layout of a sensor device according to the invention for sensing the position of a transverse crease line.
Figure 4:
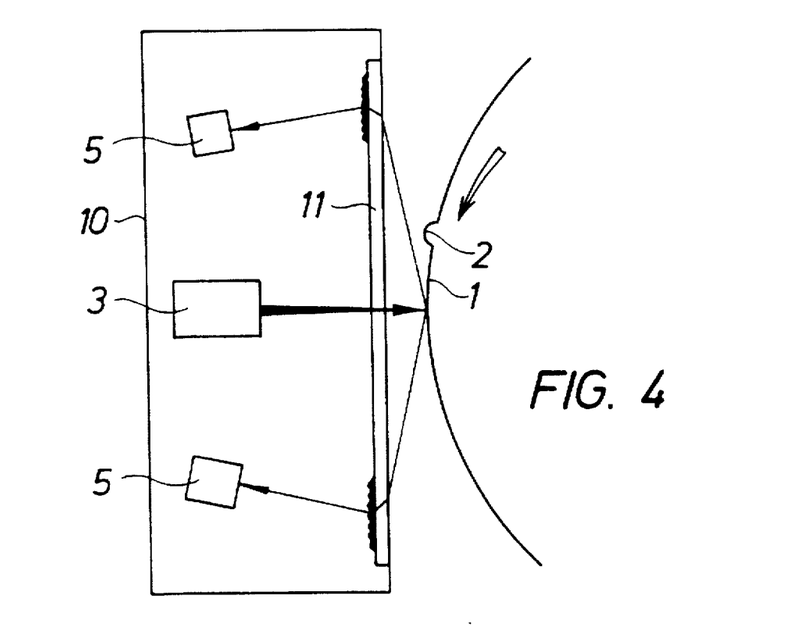

FIGS. 3 and 4 show fairly schematical the construction of two examples of the optical part of a device according to the invention.

As appears from FIG. 3, the different means shown in FIG. 1, namely the laser 3, the lense 4, the photo detectors 5, and the lenses 6, are arranged in a box 7. The light beams reflected from the packaging web 1 with its crease line 2 enters the box 7 through windows 8 and are thrown against the photo detectors 5 by means of mirrors 9. In a practical case the box 7 can be arranged at a distance of 12 mm from the packaging web 1.

In the embodiment according to FIG. 4 the laser 3 and the photo detectors 5 are arranged in a box 10, where a holographic optical element 11 is utilized for focusing and collecting light. The advantage with this solution is that a very compact optical device or sensor is achieved and that only a few optical elements are needed. This solution is accordingly well apted at a manufacture of many devices.

In the optical device or sensor it is alternatively possible to use prisms, fresnel optics or light conductors.

It is rather difficult to determine the exact position for the sensed crease line by means of the electrical signals from the two photo detectors 5. The signals contain much fuss or noise, especially from the paper structure. The crease lines are also fairly undefined, of different sizes and in certain cases unsymmetrical. The measuring signals also depend on the paper quality used.

The electrical signals from the two photo detectors 5 are treated electronically. It is obvious that the electronic equipment for this signal treatment can be made in different ways, and a certain device will be treated broadly below under reference to FIG. 6.

The first step in the signal treatment is to create a difference signal from the two photo detectors 5 for decreasing the noise from the paper structure. A further improvement in the noise level is achieved by means of the further step to form a quotient of the difference signal mentioned above and the sum signal from the two photo detectors.

Also after these operations the crease signal is rather noisy, and there are hardly any clear, easily definable flanks to trig on. However, it appears that all crease signals have certain common characteristics in their appearances. Namely, a crease signal has the general shape of an inclined N, where the distance between a positive top and a negative bottom, i.e. the two extremes of the crease signal, depends on the width of the crease line, namely in a practical case 1.8 mm.

This fact means that it is possible by means of a correlation method to asses the position of a crease line with a very good accuracy. All measurements collected at the passage of the crease line are used at the correlation method. The noise can in this way be reduced.

The principle for this correlation method is that the attained measuring signal is compared with a reference signal stored in the electronic equipment and that the correlation between the measuring signal and the reference signal is computed. Different algorithms can be utilized in the correlation method. The algorithm chosen here gives as a result a correlation factor, which is zero or negative, if no correlation can be found, and positive, if a correlation exists. Maximum correlation is at hand, when a correlation curve or signal reaches a maximum.

In the present case the per se continuous measuring signal is sampled with certain intervals. The sampled measuring signal is compared or correlated in the electronic equipment with the stored reference signal. The correlation signal will have a maximum, when the measuring signal to the greatest possible extent corresponds to the reference signal. Due to the length of the reference area the top of the correlation signal will be displaced in time in relation to the measuring signal. The position of the maximum gives the distance to the center of the crease line, counted in the number of samples.

Figure 5:
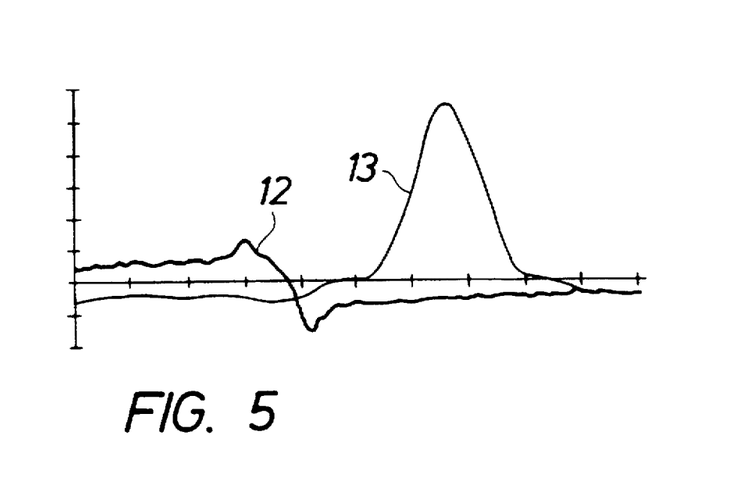
FIG. 5 is a graphical representation of a crease signal and a correlation signal.

The appearance of a measuring signal or crease signal 12 and a correlation signal 13 displaced in time in relation thereto is shown graphically in FIG. 5. In a practical embodiment a measuring wheel coupled to the packaging web 1 gives measuring pulses or sample pulses to the electronic equipment. The feed length between the pulses is determined to be 80 μm (but can be varied at will), which gives a distance between the center of the real crease line on the packaging web 1 and the signal out from a signal processor indicating the crease line of 2.88 mm.

Figure 6:
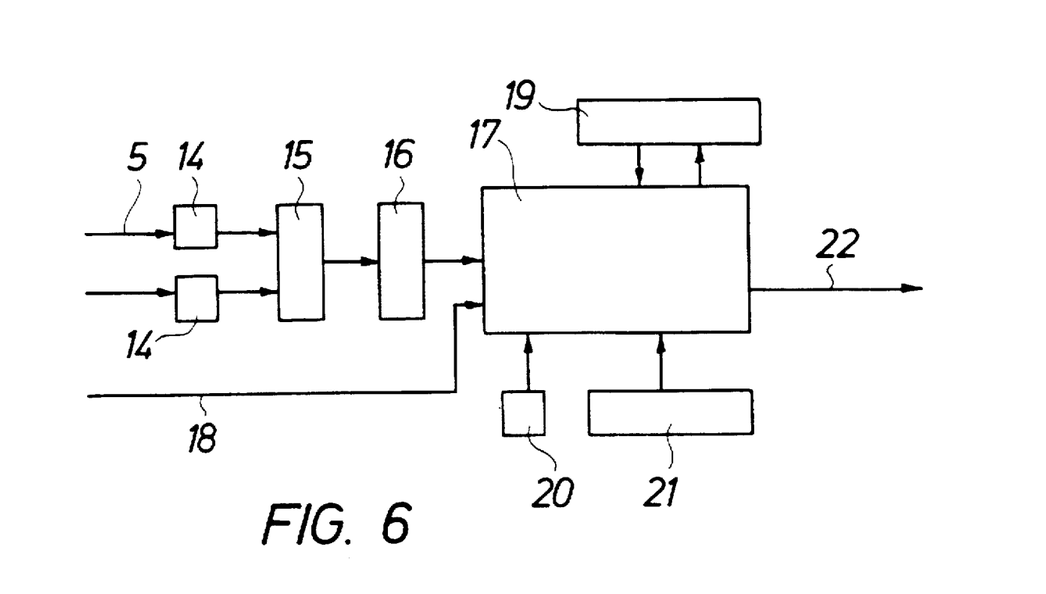
FIG. 6 is a block diagram of a signal processor chosen as an example of an embodiment, FIG. 7 in a way corresponding to FIG. 1 illustrates an optical layout of a sensor device according to the invention for sensing the position for a longitudinal crease line.

It has earlier been stated that signal treatment can occur in any electronic equipment, and a person skilled in the art can find many different solutions. One example of a block diagram useful for the purpose is shown in FIG. 6.

The signals from each of the two photo detectors 5 are fed to an S/H unit 14 ("Sample and Hold"), further to a common multiplexer 15 and an analog/digital converter 16 and finally to a digital signal processor 17. The pulses 18 from the measuring wheel of the packaging web are also fed to this unit 17. A RAM 19, an oscillator 20 and an EPROM 21 are also connected to this unit 17. A crease sensing signal 22 is fed from the unit 17.

Figure 7:
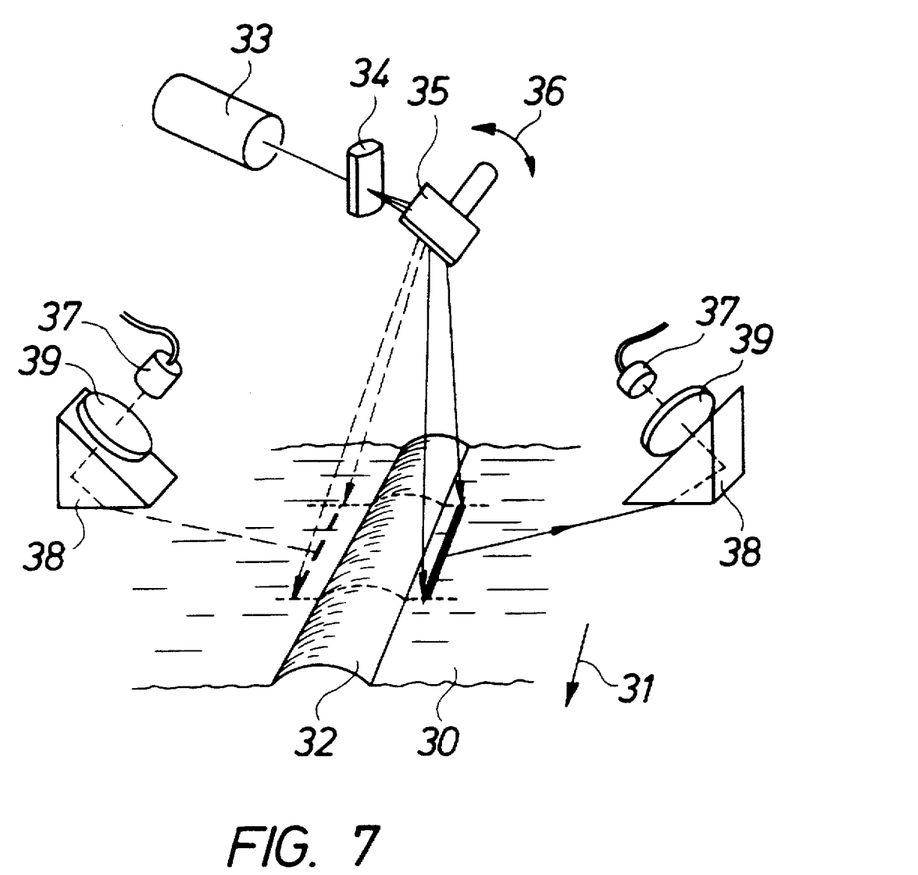

In FIG. 7 the reference numeral 30 indicates a packaging web, which is given a movement in the direction of an arrow 31 in a way not described. The packaging web 30 has a longitudinal crease line 32, the position in the transverse direction of which it is desired to determine with great precision. Reference is made to the description above with regard to information about the nature of the packaging web and the crease line.

A light diode 33 or similar light source directs its light through a lens 34 (or a group of lenses)—for creating a slot formed beam of light—on a mirror 35, which as indicated by an arrow 36 is given an oscillating movement with a high frequency, for example several kHz, so that a certain area of the packaging web 30 is swept by the beam of light in a rapidly oscillating movement.

The light thereby reflected from the packaging web 30 with its crease line 32 is sensed by means of two photo detectors or photo diodes 37, to which the light is brought and focused by means of prisms 38 and lenses 39. The sensors consisting of the photo detectors 37, prisms 38 and lenses 39 are arranged in the transverse direction of the packaging web.

The signals from the photo detectors 37 are electronically treated in a similar way as has been described above under reference to FIGS. 1–6.

It can be noted that prisms can be used in embodiments corresponding to those according to FIGS. 3 and 4 at the sensing of transverse crease lines.

Figure 8:
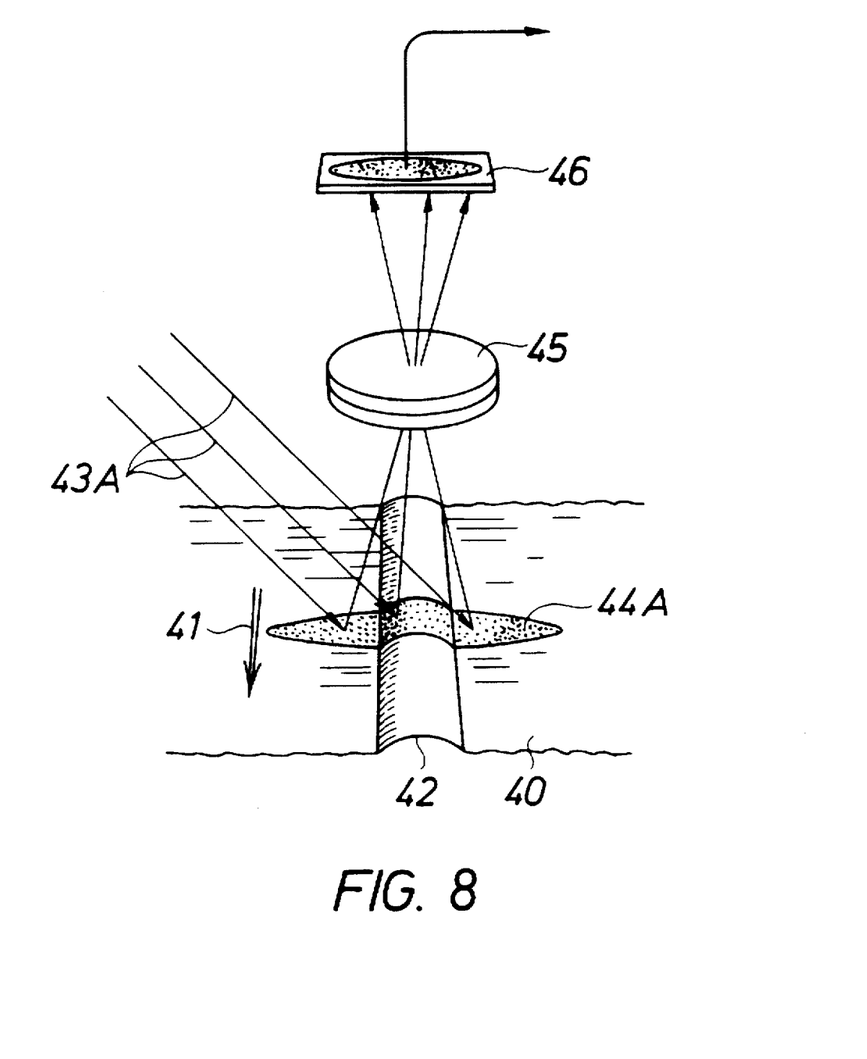
FIGS. 8 and 10 illustrate the optical layout in two working conditions of a modified sensor device for sensing the position of a longitudinal crease line.
Figure 10:
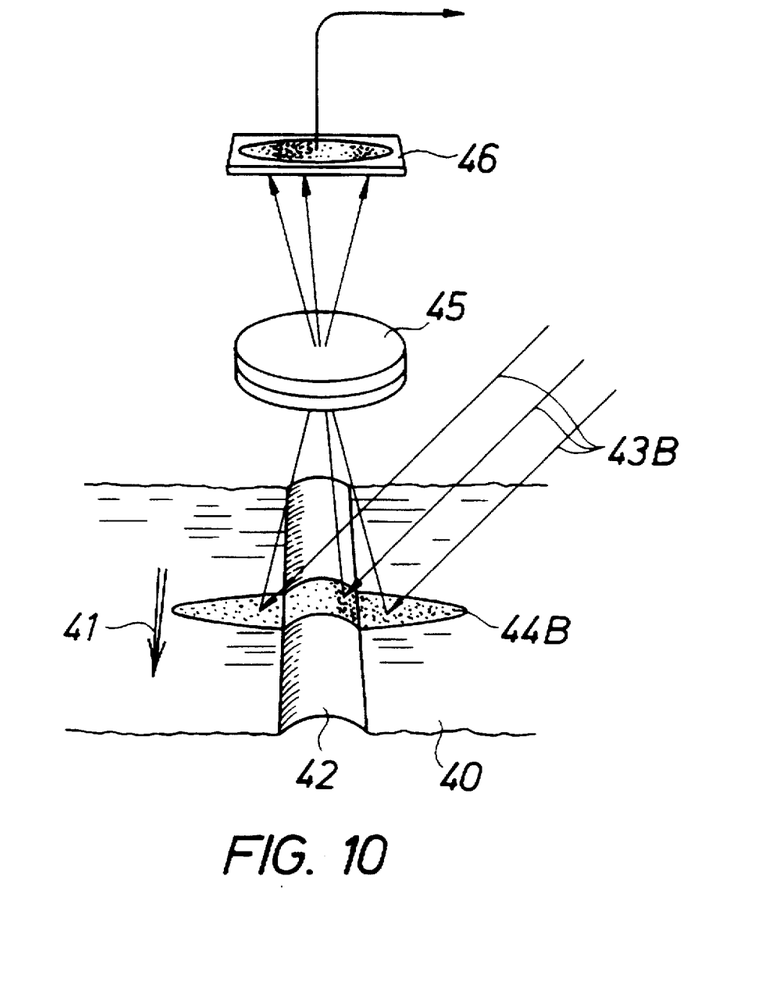

An alternative embodiment for sensing a longitudinal crease line is shown in FIGS. 8 and 10, which are to be seen together and illustrate two working conditions. A packaging web 40 is given a movement in the direction of an arrow 41 in a way not described. The packaging web 40 has a longitudinal crease line 42, the position in transverse direction of which it is desired to determine with great precision. Again, reference is made to the description above with regard to information about the nature of the packaging web and the crease line.

Contrary to all the earlier embodiments, where the light is thrown perpendicularly against the packaging web, the light is here thrown obliquely against the packaging web 40 from two directions perpendicular to the movement direction of the web. In FIG. 8 light 43A from a light source (not shown), preferably light diodes, is thrown from the left obliquely against the area for the crease line 42, while in FIG. 10 light 43B from a corresponding light source is thrown obliquely from the right against the same area. The angles of incidence against the paper can be about 50°. Light from the two directions can alternate with a very high frequency, perhaps several kHz.

The light fields 44A and 44B, respectively, generated on the packaging web 40 preferably have the form of a slot or of ellipses in the transverse direction of the web and thus transverse to the longitudinal crease line 42. The length of the slot shall cover the width of the crease line and an area outside the same, i.e. a "scan area". In practice the length of the slot can be about 30 mm.

A reflected image of the light fields 44A and 44B is alternatingly thrown through a lens 45 (i.e. in practice a lens group) to a photo detector 46. This photo detector can be of the type detector matrix, preferably with signal treatment possibility directly on the chip. A usual CCD-array can also be used.

Figure 9:
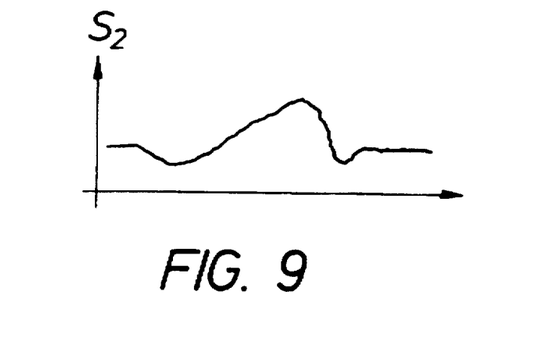
FIGS. 9 and 11 are graphical representations of crease signals from the sensor device in the working conditions according to FIGS. 8 and 10, respectively.
Figure 11:
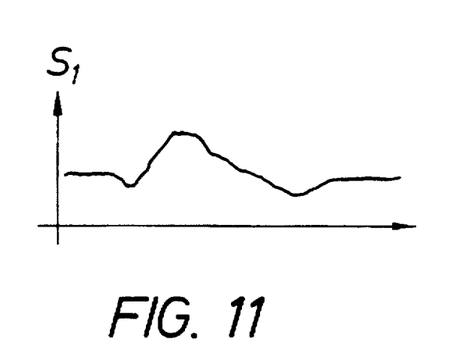
Figure 12:
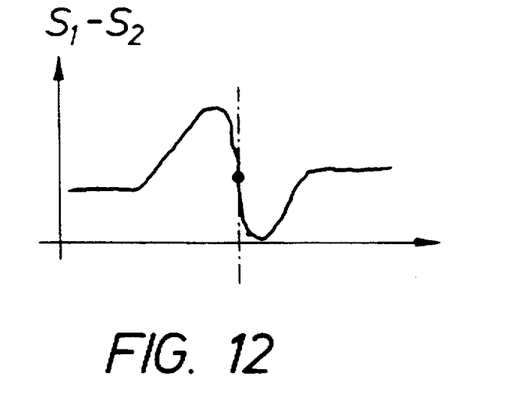
FIG. 12 is a graphical representation of the difference signal of the two crease signals according to FIGS. 9 and 11.

The signal or "picture" emanating from the photo detector 46 at light thrown from the left in FIG. 8 can have the appearance according to FIG. 9, whereas the corresponding signal at light thrown from the right according to FIG. 10 can have the appearance shown in FIG. 11. By subtracting the foregoing signal from the latter a differential signal with an appearance for example as shown in FIG. 12 can be created.

In order to determine the position of the crease line 42 the same correlation method as described above for the transverse crease line is now employed.

It should in this connection be noted that the electronics at a transverse crease line as well as a longitudinal crease line can be "self-learning", which means that crease signals fed after each other are added to the original reference signal, so that the latter thereby gradually will give an increasingly better picture of actual crease signals.

In the embodiment illustrated in FIGS. 8 and 10 light is alternatingly thrown with high frequency from the left and from the right. As an alternative it is possible to have two arrangements close to each other along the crease line, of which one arrangement creates a signal corresponding to the light thrown from the left and the other arrangement a signal corresponding to the light thrown from the right. The light sources can hereby of course transmit continuous light.

The embodiments described under reference to FIGS. 7–12 for sensing a longitudinal crease line can also in relevant parts be used as alternatives to the embodiments described under reference to FIGS. 1–4 for sensing a transverse crease line.

The amount of light reflected from the photo detectors of the devices is determined by:

the absorption the index of refraction the surface topography the glossiness (i.e. micro topography parameter) of the packaging web or the surface.

If the material is transparent, also the optical characteristics of the lower surface will have effect.

The method of sensing the position of the crease line according to the present invention minimizes the influence of changes in absorption, index of refraction, micro topograhpy and glossiness as well as changes in topography along the crease line. Only topography changes transverse to the crease line, i.e. the shape of the crease line itself, will have full effect in the signal.

The end shape of a package is characterized by the fold notches created in the packaging material, i.e. the crease lines. If a crease pattern is used as position reference at cutting, application and other processes, the positioning of these can be performed with a greater precision. In this way the discarding is reduced and the variation in the function and appearance of the packages is decreased.

I claim:

1. A method for determining the position of a crease line or similar embossment in a moving packing web, the steps comprising;
   (a) directing at least one light beam perpendicularly against the surface of said moving packing web,
   (b) detecting two reflected lights from said at least one light beam as reflected from said moving packing strip at oblique angles to, and on either side of, said at least one light beam,
   (c) creating an electrical signal characteristic of each said two reflected lights,
   (d) converting and combining each of said electrical signals to form a measuring signal,
   (e) comparing said measuring signal to a reference signal representative of a reference crease line, and
   (f) determining the position of said crease line or similar embossment in said moving packing web, as being where the correlation between said measuring signal and said reference signal is at a maximum.

2. A method for determining the position of a crease line or similar embossment in a moving packing web, according to claim 1, in which said light beam is an oscillating light beam.

3. A method for determining the position of a crease line or similar embossment in a moving packing web, according to claim 1, in which said light beam is a laser light beam in the shape of a slot transverse to a direction of movement of said moving packing web.

4. A method for determining the position of a crease line or similar embossment in a moving packing web, according to claim 1, in which said reflected lights are detected by photo detectors.

5. A method for determining the position of a crease line or similar embossment in a moving packing web, according to claim 1, in which said reflected lights are reflected at angles to said at least one light beam of more than 30°.

6. A method for determining the position of a crease line or similar embossment in a moving packing web, according to claim 1, in which said measuring signal is sampled with a predetermined feeding length of said packing web as a basis.

7. A method for determining the position of a crease line or similar embossment in a moving packing web, according to claim 1, in which said two reflected lights are symmetrical with respect to said at least one light beam.

8. A method for determining the position of a crease line or similar embossment in a moving packing web, according to claim 7, in which said one light beam is an oscillating light beam.

9. A method for determining the position of a crease line or similar embossment in a moving packing web, according to claim 7, in which said one light beam is a laser light beam in the shape of a slot transverse to a direction of movement of said moving packing web.

10. A method for determining the position of a crease line or similar embossment in a moving packing web, according to claim 7, in which each of said two reflected lights are detected by an individual photo detector.

11. A method for determining the position of a crease line or similar embossment in a moving packing web, according to claim 1, in which each of said two reflected lights are reflected at an angle to said light beam of more than 30° on each side thereof.

12. A method for determining the position of a crease line or similar embossment in a moving packing web, according to claim 1, in which said measuring signal is a quotient between the difference between the two electrical signals and the sum thereof.

13. A method for determining the position of a crease line or similar embossment in a moving packing web, according to claim 1, in which two said light beams are directed obliquely against a point on said surface of said moving packing web, from opposite directions at equal angles to a line perpendicular to said point on said surface of said moving packing strip, such that each said light beam will cause a said reflected light, each of said reflected lights being reflected substantially perpendicularly away from said surface of said moving packing strip and generally aligned with each other.

14. A method for determining the position of a crease line or similar embossment in a moving packing web, according to claim 13, in which both of said reflected lights are detected by a photo detector array disposed in a substantially perpendicular relationship to said moving packing strip.

15. A method for determining the position of a crease line or similar embossment in a moving packing web, the steps comprising;
   (a) directing light beam perpendicularly against the surface of said moving packing web,
   (b) detecting a first reflected light from said light beam as reflected from said moving packing strip at a first oblique angle to said light beam, and creating a first electrical signal characteristic of said first reflected light,
   (c) detecting a second reflected light from said light beam as reflected from said moving packing strip at a second oblique angle to said light beam, and creating a second electrical signal characteristic of said second reflected light,
   (d) combining said first and second electrical signal to create a measuring signal,
   (e) comparing said measuring signal to a reference signal representative of a reference crease line, and
   (f) determining the position of said crease line or similar embossment in said moving packing web, as being where the correlation between said measuring signal and said reference signal is at a maximum.

16. Apparatus for determining the position of a crease line or similar embossment in a moving packing web, said apparatus comprising;
   (a) a light source for directing at least one light beam against the surface of said moving packing web,
   (b) at least one means for detecting reflected light from said at least one light beam reflected from said moving packing strip at an oblique angle to said at least one light beam, and for creating an electrical signal characteristic of said reflected light,
   (c) a signal processor for creating a measuring signal representative of said reflected light, and comparing said measuring signal to a reference signal representative of a reference crease line, and
   (d) said crease line or similar embossment in said moving packing web, being where the correlation between said measuring signal and said reference signal is at a maximum.

17. Apparatus for determining the position of a crease line or similar embossment in a moving packing web, according to claim 16, in which said light source directs a single light beam against the surface of said moving packing web at an angle substantially perpendicular to said moving packing web, and said at least one means for detecting reflected light comprises two means for detecting reflected light from said one light beam, a first for detecting a first reflected light and creating a first electrical signal representative of said first reflected light, and a second for detecting a second reflected light and creating a second electrical signal representative of said second reflected light, and said signal processor create said measuring signal by combining said first and second electrical signals.

18. Apparatus for determining the position of a crease line or similar embossment in a moving packing web, according to claim 17, in which said single light beam is a laser light beam in the shape of a slot transverse to the direction of movement of said moving packing web.

19. Apparatus for determining the position of a crease line or similar embossment in a moving packing web, according to claim 16, in which at least two light sources are provided to direct a pair of light beams against the surface of said moving packing web at equal oblique angles to a point on said surface of said moving packing web, from opposite directions at equal angles to a line perpendicular to said point, and said at least one means for detecting reflected light comprises a single means for detecting reflected light reflected perpendicularly from said point on said surface of said moving packing web.

20. Apparatus for determining the position of a crease line or similar embossment in a moving packing web, according to claim 19, in which said single means for detecting reflected light reflected perpendicularly from said point on said surface of said moving packing web is adapted to detect two reflected lights aligned with each other.

* * * * *